United States Patent
Chirik et al.

(10) Patent No.: US 11,001,667 B2
(45) Date of Patent: May 11, 2021

(54) OLIGOMERIC AND POLYMERIC SPECIES COMPRISING CYCLOBUTANE UNITS

(71) Applicant: The Trustees of Princeton University, Princeton, NJ (US)

(72) Inventors: Paul J. Chirik, Princeton, NJ (US); C. Rose Kennedy, Princeton, NJ (US); Sarah Tondreau, Los Alamos, NM (US)

(73) Assignee: THE TRUSTEES OF PRINCETON UNIVERSITY, Princeton, NJ (US)

(*) Notice: Subject to any disclaimer, the term of this patent is extended or adjusted under 35 U.S.C. 154(b) by 0 days.

(21) Appl. No.: 16/239,938

(22) Filed: Jan. 4, 2019

(65) Prior Publication Data

US 2019/0211142 A1  Jul. 11, 2019

Related U.S. Application Data

(60) Provisional application No. 62/614,022, filed on Jan. 5, 2018.

(51) Int. Cl.
| | |
|---|---|
| *C08G 61/04* | (2006.01) |
| *B01J 31/18* | (2006.01) |
| *C08F 136/04* | (2006.01) |
| *C07C 2/46* | (2006.01) |

(52) U.S. Cl.
CPC ............ C08G 61/04 (2013.01); B01J 31/183 (2013.01); B01J 31/1805 (2013.01); B01J 31/1815 (2013.01); C07C 2/465 (2013.01); C08F 136/04 (2013.01); *B01J 2231/12* (2013.01); *B01J 2231/125* (2013.01); *B01J 2231/20* (2013.01); *B01J 2531/0244* (2013.01); *B01J 2531/0294* (2013.01); *B01J 2531/842* (2013.01); *B01J 2531/845* (2013.01); *B01J 2531/847* (2013.01); *C07C 2531/22* (2013.01); *C07C 2601/04* (2017.05); *C08G 2261/3323* (2013.01); *C08G 2261/362* (2013.01)

(58) Field of Classification Search
CPC .............................. C08G 61/04; B01J 31/183
See application file for complete search history.

(56) References Cited

U.S. PATENT DOCUMENTS

2009/0281245 A1* 11/2009 MacKinnon ........... C08J 5/2268
525/200

OTHER PUBLICATIONS

Hall et al., "Bicyclobutanes and Cyclobutenes: Unusual Carbocyclic Monomers," J. Polym. Sci.: Part A: Polym. Chem., vol. 41, 625-635 (2003). (Year: 2003).*

Hill et al., "gem-Dimethyl Effect in a Grignard Reagent Cyclization-Cleavage Rearrangement," J. Org. Chem., 1981, 46, 1177-1182. (Year: 1981).*

(Continued)

*Primary Examiner* — Catherine S Branch
(74) *Attorney, Agent, or Firm* — J. Clinton Wimbish; Nexsen Pruet PLLC

(57) ABSTRACT

In one aspect, oligomeric and polymeric species are described herein exhibiting new architectures and associated properties. In some embodiments, such species are synthesized by oligomerization or polymerization of diene monomer via cycloaddition in the presence of a transition metal complex. Oligomers described herein, for example, comprise cyclobutane units in the oligomer backbone. Similarly, a polymers described herein comprise cyclobutane units in the polymer backbone.

34 Claims, 2 Drawing Sheets

(56) References Cited

OTHER PUBLICATIONS

Takeuchi et al., "Selective cyclopolymerization of α-ω-dienes and copolymerization with ethylene catalyzed by Fe and Co complexes," Dalton Trans., 2009, 8955-8962. (Year: 2009).*
Goldmann et al., "Post-Functionalization of Polymers via Orthogonal Ligation Chemistry," Macromol. Rapid. Commun., 2013, 34, 810-849. (Year: 2013).*

* cited by examiner

OLIGOMERIC AND POLYMERIC SPECIES COMPRISING CYCLOBUTANE UNITS

RELATED APPLICATION DATA

The present application claims priority pursuant to 35 U.S.C. § 119(e) to U.S. Provisional Patent Application Ser. No. 62/614,022 filed Jan. 5, 2018 which is incorporated herein by reference in its entirety.

FIELD

The present invention relates to oligomers and polymers and, in particular, to oligomers and polymers comprising cyclobutane units in the oligomer or polymer backbone.

BACKGROUND

Conjugated dienes are typically polymerized by free radical, anionic or transition metal-mediated 1,2- or 1,4- addition to faun branched or linear polymers, respectively. As a result of few polymerization options, the potential for development of new oligomeric and polymeric species from diene monomers is limited.

SUMMARY

In one aspect, oligomeric and polymeric species are described herein exhibiting new architectures and associated properties. In some embodiments, such species are synthesized by oligomerization or polymerization of diene monomer via cycloaddition in the presence of a transition metal complex. Oligomers described herein, for example, comprise cyclobutane units in the oligomer backbone. Similarly, polymers described herein comprise cyclobutane units in the polymer backbone.

In another aspect, methods of polymerization are also described. A method of polymerization comprises providing a reaction mixture including a diene monomer component and polymerizing the diene monomer component in the presence of a transition metal complex or derivative thereof to provide a polymer, wherein the transition metal complex is of Formula (I):

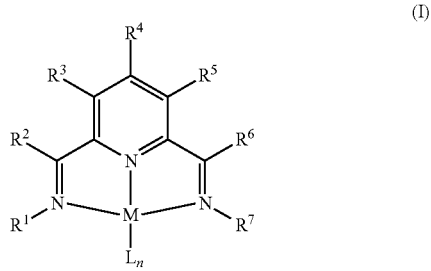

(I)

wherein M is selected from the group consisting of iron, cobalt and nickel and wherein $R^1$-$R^7$ are independently selected from the group consisting of hydrogen, alkyl, heteroalkyl, cycloalkyl, heterocycloalkyl, aryl and heteroaryl, wherein the alkyl, heteroalkyl, cycloalkyl, heterocycloalkyl, aryl and heteroaryl are optionally substituted with one or more substituents selected from the group consisting of $(C_1$-$C_{10})$-alkyl, $(C_1$-$C_{10})$-alkenyl, alkoxy, halo and hydroxyl; and wherein L is selected from the group consisting of halo, $N_2$, alkene/diene, carboxylate and CO, and n is 1 or 2. As described herein, polymerization of the diene monomer may proceed via cycloaddition with the transition metal complex serving as catalyst.

The resulting polymer comprises cyclobutane units in the polymer backbone. In some embodiments, the cyclobutane units are directly bonded to one another in the backbone. Alternatively, the cyclobutane units can be separated by one or more methylenes in the polymer backbone. Moreover, oligomers comprising cyclobutane units in the oligomer backbone can be synthesized according to the foregoing method wherein diene monomer is limited to the desired oligomer chain length and/or the polymerization is otherwise terminated at the desired oligomer chain length.

These and other embodiments are described in further detail in the detailed description which follows.

BRIEF DESCRIPTION OF THE DRAWINGS

FIG. 1(*b*) illustrates incorporation of atoms from adjacent diene monomers into a cyclobutane unit according to some embodiments.

DETAILED DESCRIPTION

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

Definitions

The term "alkyl" as used herein, alone or in combination, refers to a straight or branched saturated hydrocarbon group optionally substituted with one or more substituents. For example, an alkyl can be $C_1$-$C_{30}$.

The term "alkene" or "alkenyl" as used herein, alone or in combination, refers to a straight or branched chain hydrocarbon group having at least one carbon-carbon double bond and optionally substituted with one or more substituents The term "aryl" as used herein, alone or in combination, refers to an aromatic monocyclic or multicyclic ring system optionally substituted with one or more ring substituents.

The term "heteroaryl" as used herein, alone or in combination, refers to an aromatic monocyclic or multicyclic ring system in which one or more of the ring atoms is an element other than carbon, such as nitrogen, oxygen and/or sulfur.

The term "cycloalkyl" as used herein, alone or in combination, refers to a non-aromatic, mono- or multicyclic ring system optionally substituted with one or more ring substituents.

The term "heterocycloalkyl" as used herein, alone or in combination, refers to a non-aromatic, mono- or multicyclic ring system in which one or more of the atoms in the ring system is an element other than carbon, such as nitrogen, oxygen or sulfur, alone or in combination, and wherein the ring system is optionally substituted with one or more ring substituents.

The term "heteroalkyl" as used herein, alone or in combination, refers to an alkyl moiety as defined above, having one or more carbon atoms in the chain, for example one, two or three carbon atoms, replaced with one or more heteroatoms, which may be the same or different, where the point of attachment to the remainder of the molecule is through a carbon atom of the heteroalkyl radical.

The term "alkoxy" as used herein, alone or in combination, refers to the moiety RO—, where R is alkyl or alkenyl defined above.

The term "halo" as used herein, alone or in combination, refers to elements of Group VIIA of the Periodic Table (halogens). Depending on chemical environment, halo can be in a neutral or anionic state.

I. Oligomers and Polymers

Figure 1A:
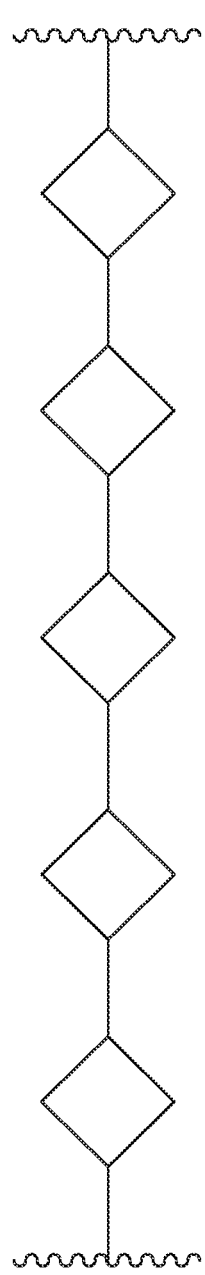
FIG. 1(*a*) illustrates a polymer comprising cyclobutane units according to some embodiments.
Figure 1B:
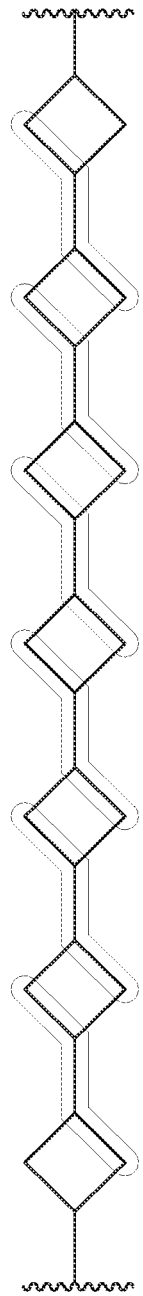

Oligomers and polymers comprising cyclobutane units in the oligomer or polymer backbone are described herein. In forming part of the backbone, the cyclobutane units are not pendant groups. FIG. 1(a) illustrates a polymer comprising cyclobutane units in the polymer backbone according to some embodiments. In the embodiment of FIG. 1(a), the cyclobutane units exhibit a 1,3-incorporation into the polymer backbone. Moreover, the cyclobutane units are directly linked with one another. In other embodiments, the linked cyclobutane units can exhibit a 1,2-incorporation into the polymeric backbone. A mixture of 1,3-incorporation and 1,2-incorporation of cyclobutane units is also possible. As described further herein, the embodiment of FIG. 1(a) can be synthesized via cycloaddition polymerization of 1,3-butadiene in the presence of transition metal complex. Cyclobutane units of the polymer, for example, incorporate atoms from linked butadiene monomers, as illustrated in FIG. 1(b).

Figure 2:
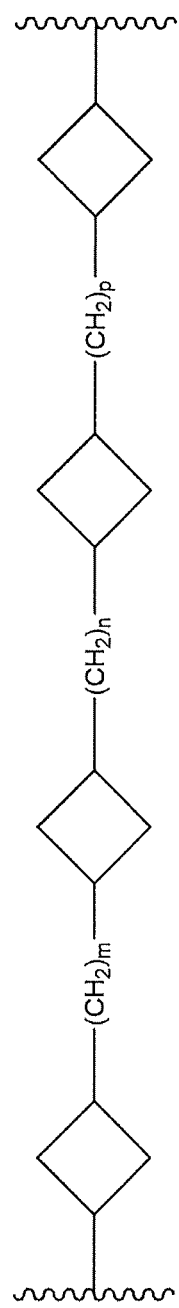
FIG. 2 illustrates a polymer comprising cyclobutane units according to some embodiments.

FIG. 2 illustrates another embodiment of a polymer comprising cyclobutane units in the polymer backbone. In the embodiment of FIG. 2, the cyclobutane units are separated by one or more methylene groups. Depending on identity of the diene monomer component, m, n and p can be the same or can vary from one another. In some embodiments, m, n and p are independently selected from 0-10. Additionally, the cyclobutane units may be separated by one or more heteroatoms or heteroatom moieties (O, NR, SiR$_2$, etc.). In further embodiments, the cyclobutane units may be separated by one more ring structures, such as cycloalkyl or heterocycloalkyl. Any combination of methylene groups, heteroatoms and/or ring structures may also separate the cyclobutane units.

Polymeric species comprising cyclobutane units in the polymer backbone may also exhibit tacticity. Depending on specific identity of the diene monomer component and/or transition metal complex, the resulting polymer can be isotactic, syndiotactic or atactic. In some embodiments, polymeric species described herein can also comprise one or more pendent groups. Pendent groups, for example, can comprise alkyl or alkenyl moieties. Substituted diene monomer can be employed to incorporate pendant groups into the polymer. In some embodiments, isoprene or 2-vinyl-1,3-butadiene monomer can result in polymer comprising alkyl and alkenyl pendant groups, respectively. The pendent groups can provide additional functionality for cross-linking or altering chain packing and/or crystallinity. In some embodiments, polymers described herein are entirely aliphatic.

Chain ends of polymeric species described herein can exhibit reactive moieties or functionalities permitting incorporation of the polymer into various architectures including, but not limited to, block copolymers, graft copolymers and/or crosslinked structures. In other embodiments, chain ends can comprise a capping agent. The capping agent may provide orthogonal protection for reaction specificity and/or self-assembled architectures comprising the polymer. Capping agents can also be chemical modified to impart various functionalities including hydroxyl, amine, carboxyl or glycol moieties. In some embodiments, capping agents are coupled to one or more polymer ends via hydrofunctionalization including, but not limited to, hydroboration, hydrosilylation and hydroformylation.

Notably, oligomers can have any of the foregoing properties described herein for polymeric species. Oligomers can have any desired chain length. In some embodiments, for example, an oligomer incorporates as little as 2 to 5 cyclobutane units.

II. Methods of Oligomerization/Polymerization

In another aspect, methods of polymerization are also described. A method of polymerization comprises providing a reaction mixture including a diene monomer component and polymerizing the diene monomer component in the presence of a transition metal complex or derivative thereof to provide a polymer, wherein the transition metal complex is of Formula (I):

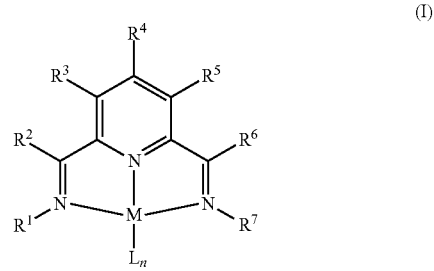

wherein M is selected from the group consisting of iron, cobalt and nickel and wherein R$^1$-R$^7$ are independently selected from the group consisting of hydrogen, alkyl, heteroalkyl, cycloalkyl, heterocycloalkyl, aryl and heteroaryl, wherein the alkyl, heteroalkyl, cycloalkyl, heterocycloalkyl, aryl and heteroaryl are optionally substituted with one or more substituents selected from the group consisting of (C$_1$-C$_{10}$)-alkyl, (C$_1$-C$_{10}$)-alkenyl, alkoxy, halo and hydroxyl; and wherein L is selected from the group consisting of halo, N$_2$, alkene/diene, carboxylate and CO, and N$_2$ and n is 1 or 2. As described herein, polymerization of the diene monomer may proceed via cycloaddition with the transition metal complex serving as catalyst. The resulting polymer comprises cyclobutane units in the polymer backbone. Moreover, the resulting polymer can have any properties described in Section I herein.

The diene monomer component of the reaction mixture can comprise conjugated diene such as 1,3-butadiene and/or substituted 1,3-butadiene. Alternatively, the diene monomer component can comprise non-conjugated diene or a mixture of conjugated diene and non-conjugated diene. Specific composition of the diene monomer component can be selected according to the desired structure and properties of the polymer.

In some embodiments, the transition metal complex of Formula (I) is provided to the reaction mixture under an inert atmosphere due to air and/or moisture sensitivity of the complex. The transition metal complex may also be formed in situ. Bench stable precursor, such as MX$_2$ (M=Fe, Co or Ni and X=halo, pseudohalide, sulfonate, etc.) can be added to the reaction mixture along with PDI [bis(imino)pyridine] ligand and reductant (RMgX, RLi, NaBHEt$_3$, Mg, AlR$_3$, etc.) to generate the transition metal complex in situ. Optionally, initiator and/or chain terminating agent may also be added to the reaction mixture.

Oligomers comprising cyclobutane units in the oligomer backbone can be synthesized according to the foregoing method wherein diene monomer is limited to the desired oligomer chain length and/or the polymerization is otherwise terminated at the desired oligomer chain length.

These and other embodiments are further illustrated by the following non-limiting example.

Example 1—Diene Polymerization

Under an inert atmosphere, a high-pressure reaction vessel was primed with precatalyst (PDIFe(N$_2$)$_{n=1,2}$ or PDIFe (diene) where PDI describes generic substituted pyridine-2,6-diimine ligand). Optionally, hydrocarbon solvent may be added. The head-space of the vessel was evacuated, and 1,3-butadiene monomer was added by a calibrated gas addition or by vacuum transfer of a known mass of liquid reagent. Optionally, initiator and/or chain-terminating agent (α-olefins or branched conjugated dienes) may also be added. The reaction was maintained with mixing until complete consumption of the monomer occurred or the desired chain length was obtained. The volatile reaction components were removed by vacuum transfer. The non-volatile residue was diluted with solvent and either a) passed through a short plug of silica and concentrated in vacuo, or b) precipitated from solution with the addition of an antisolvent and collected by filtration. The resulting polymeric material is dried under vacuum.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. An oligomer comprising:
cyclobutane units in the oligomer backbone, wherein the cyclobutane units comprise a mixture of 1,2-cyclobutane and 1,3-cyclobutane.

2. The oligomer of claim 1, wherein the cyclobutane units are directly bonded to one another in the oligomer backbone.

3. The oligomer of claim 1, wherein the cyclobutane units are separated by one or more methylenes in the polymer backbone.

4. The oligomer of claim 1 comprising 2 to 5 cyclobutane units.

5. The oligomer of claim 1, wherein the oligomer is entirely aliphatic.

6. The oligomer of claim 1 further comprising one or more pendant groups.

7. The oligomer of claim 6, wherein the pendant groups comprise alkyl or alkenyl moieties.

8. A polymer comprising:
cyclobutane units in the polymer backbone, wherein the polymer is entirely aliphatic and wherein the polymer comprises one or more pendant groups comprising alkyl or alkenyl moieties.

9. The polymer of claim 8, wherein the cyclobutane units are directly bonded to one another in the polymer backbone.

10. The polymer of claim 8, wherein the cyclobutane units are separated by one or more methylenes in the polymer backbone.

11. The polymer of claim 8, wherein the cyclobutane units comprise 1,2-cyclobutane.

12. The polymer of claim 8, wherein the cyclobutane units comprise 1,3-cyclobutane.

13. The polymer of claim 8, wherein the cyclobutane units comprise a mixture of 1,2-cyclobutane and 1,3-cyclobutane.

14. The polymer of claim 8 further comprising a capping agent.

15. The polymer of claim 14, wherein the capping agent provides orthogonal protection.

16. A method polymerization comprising:
providing a reaction mixture including a diene monomer component; and
polymerizing the diene monomer component in the presence of a transition metal complex or derivative thereof to provide a polymer, wherein the transition metal complex is of Formula (I):

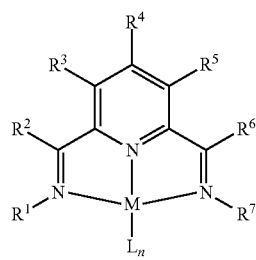

(I)

wherein M is selected from the group consisting of iron, cobalt and nickel and wherein $R^1$-$R^7$ are independently selected from the group consisting of hydrogen, alkyl, heteroalkyl, cycloalkyl, heterocycloalkyl, aryl and heteroaryl, wherein the alkyl, heteroalkyl, cycloalkyl, heterocycloalkyl, aryl and heteroaryl are optionally substituted with one or more substituents selected from the group consisting of ($C_1$-$C_{10}$)-alkyl, ($C_1$-$C_{10}$)-alkenyl, alkoxy, halo and hydroxyl; and wherein L is selected from the group consisting of halo, $N_2$, alkene/diene, carboxylate and CO, and $N_2$ and n is 1 or 2, and
wherein the polymer comprises cyclobutane units in the polymer backbone.

17. The method of claim 16, wherein the cyclobutane units are directly bonded to one another in the polymer backbone.

18. The method of claim 16, wherein the cyclobutane units are separated by one or more methylenes in the polymer backbone.

19. The method of claim 16, wherein the cyclobutane units comprise 1,2-cyclobutane.

20. The method of claim 16, wherein the cyclobutane units comprise 1,3-cyclobutane.

21. The method of claim 16, wherein the cyclobutane units comprise a mixture of 1,2-cyclobutane and 1,3-cyclobutane.

22. The method of claim 16, wherein the polymer is entirely aliphatic.

23. The method of claim 16, wherein the diene monomer component comprises conjugated diene.

24. The method of claim 16, wherein the diene monomer component comprises non-conjugated diene.

25. The method of claim 16, wherein the diene monomer component comprises a mixture of conjugated diene and non-conjugated diene.

26. The method of claim 16, wherein the transition metal complex is formed in situ.

27. The method of claim 16, wherein the polymerization proceeds via cycloaddition.

28. The method of claim 16, wherein M is iron.

29. A polymer comprising:
cyclobutane units in the polymer backbone, wherein the polymer is entirely aliphatic and the cyclobutane units are separated by one or more methylenes in the polymer backbone.

30. A polymer comprising:
cyclobutane units in the polymer backbone, wherein the polymer is entirely aliphatic and the cyclobutane units comprise a mixture of 1,2-cyclobutane and 1,3-cyclobutane.

31. An oligomer comprising:
cyclobutane units in the oligomer backbone, and one or more pendant groups comprising alkenyl moieties.

32. The oligomer of claim 31, comprising 2 to 5 cyclobutane units.

33. The oligomer of claim 31, wherein the cyclobutane units are directly bonded to one another in the oligomer backbone.

34. The oligomer of claim 31, wherein the cyclobutane units are separated by one or more methylenes in the polymer backbone.

\* \* \* \* \*